United States Patent
Abboudi et al.

(10) Patent No.: US 9,611,152 B2
(45) Date of Patent: Apr. 4, 2017

(54) SYNTHESIS METHOD OF PRECURSORS TO PRODUCE MOLYBDENUM OXIDE MOO3 AND RELATED MATERIALS

(71) Applicant: TAIBAH UNIVERSITY, Al-Madinah (SA)

(72) Inventors: Mostafa Abboudi, Al-Madinah (SA); Hicham Oudghiri Hassani, Al-Madinah (SA); Fahd Al-Wadaani, Al-Madinah (SA); Mouslim Messali, Al-Madinah (SA); Souad Rakass, Al-Madinah (SA)

(73) Assignee: TAIBAH UNIVERSITY (SA)

( * ) Notice: Subject to any disclaimer, the term of this patent is extended or adjusted under 35 U.S.C. 154(b) by 0 days.

(21) Appl. No.: 14/652,341

(22) PCT Filed: Jan. 9, 2014

(86) PCT No.: PCT/IB2014/058139
§ 371 (c)(1),
(2) Date: Jun. 15, 2015

(87) PCT Pub. No.: WO2014/108841
PCT Pub. Date: Jul. 17, 2014

(65) Prior Publication Data
US 2015/0344320 A1    Dec. 3, 2015

(30) Foreign Application Priority Data

Jan. 9, 2013 (MA) .......................................... 35555

(51) Int. Cl.
| | |
|---|---|
| C01G 39/00 | (2006.01) |
| C01G 51/00 | (2006.01) |
| C07F 11/00 | (2006.01) |
| C01G 39/02 | (2006.01) |
| B82Y 30/00 | (2011.01) |

(52) U.S. Cl.
CPC .............. C01G 51/40 (2013.01); B82Y 30/00 (2013.01); C01G 39/00 (2013.01); C01G 39/02 (2013.01); C07F 11/005 (2013.01); C01P 2002/72 (2013.01); C01P 2004/64 (2013.01); C01P 2006/12 (2013.01)

(58) Field of Classification Search
CPC ........ C01G 51/40; C01G 39/00; C01G 39/02; C07F 11/005; B82Y 30/00; C01P 2002/72; C01P 2004/64; C01P 2006/12
See application file for complete search history.

(56) References Cited

U.S. PATENT DOCUMENTS

| | | | | |
|---|---|---|---|---|
| 4,952,548 | A * | 8/1990 | Kato ................... | B01D 53/8628 423/239.1 |
| 5,968,465 | A * | 10/1999 | Koveal ................. | B01D 53/04 252/373 |
| 6,346,348 | B1 | 2/2002 | Nakajima et al. | |
| 7,829,060 | B2 | 11/2010 | Taube et al. | |
| 8,303,706 | B2 | 11/2012 | Reddy | |
| 2002/0193254 | A1 | 12/2002 | Moser et al. | |
| 2003/0116473 | A1* | 6/2003 | Koide .................... | B01J 21/12 208/217 |
| 2005/0047993 | A1 | 3/2005 | Moser et al. | |
| 2008/0017551 | A1* | 1/2008 | Kiriyama .............. | B01J 21/12 208/134 |
| 2009/0286678 | A1 | 11/2009 | Hagemeyer | |
| 2012/0230900 | A1 | 9/2012 | Saito et al. | |

FOREIGN PATENT DOCUMENTS

| | | |
|---|---|---|
| EP | 1666420 A2 | 6/2006 |
| EP | 2484633 A1 | 8/2012 |
| WO | WO-0130701 A1 | 5/2001 |

* cited by examiner

*Primary Examiner* — Anthony J Zimmer
(74) *Attorney, Agent, or Firm* — Andrew M. Calderon; Roberts Mlotkowski Safran Cole & Calderon P.C.

(57) ABSTRACT

This invention relates to precursors of the molybdenum-containing materials such as molybdenum trioxide MoO3. These precursors can be used to prepare polymetallic oxides materials varying metals proportions or they can be used for composite phases as well. Moreover, these precursors are highly soluble in polar solvents as the water or alcohols. It follows their potential to also obtain materials containing molybdenum as thin films. These precursors are obtained by solid state reaction of polycarboxylic acids and ammonium molybdate (NH4)6Mo7O24.4H2O.

26 Claims, 3 Drawing Sheets

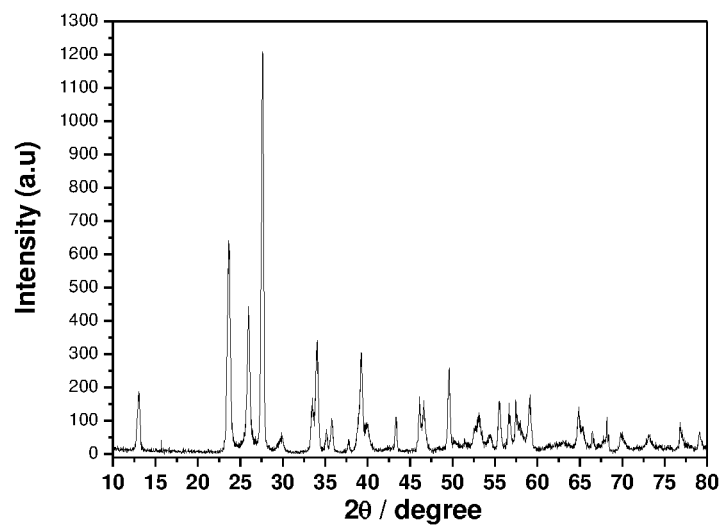
Figure1 : X rays diffraction pattern of $MoO_3$(JCPDS : 85-2405) obtained using the oxalate precursor.

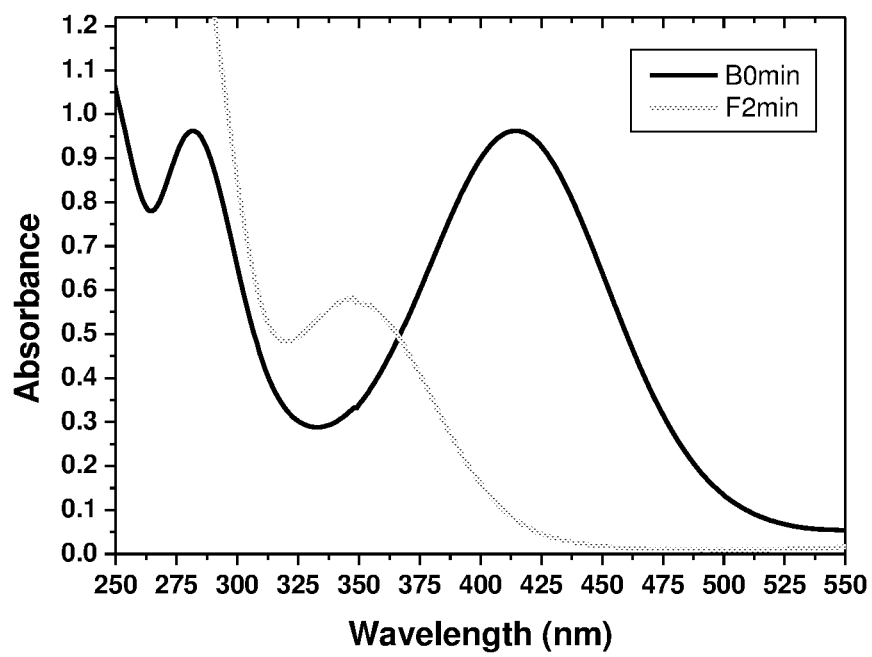
Figure 2 : Catalytic test of the reduction of 2- nitrophenol en 2-aminophenol using the obtained MoO$_3$ as catalyst.

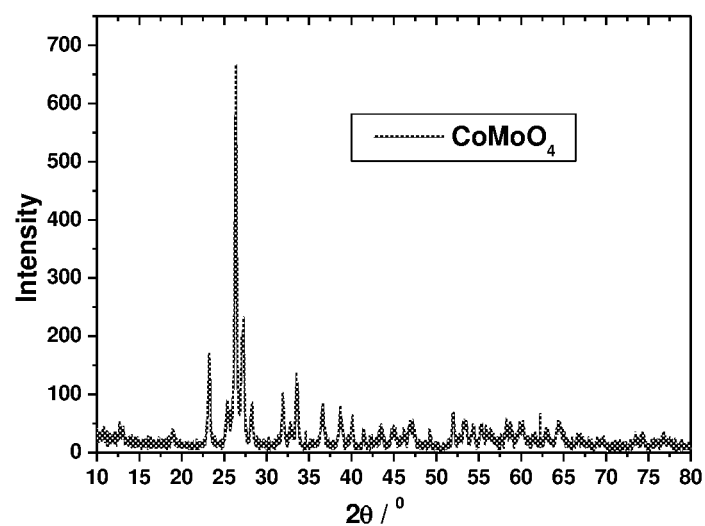
Figure 3: X rays diffraction pattern of the obtained cobalt molybdate $CoMoO_4$ according to the JCPDS card number JCPDS #21-0868

SYNTHESIS METHOD OF PRECURSORS TO PRODUCE MOLYBDENUM OXIDE MOO3 AND RELATED MATERIALS

FIELD OF THE INVENTION

The invention relates to precursors of molybdenum-containing materials.

BRIEF DESCRIPTION OF THE DRAWINGS

FIG. 1 shows an x-ray spectrum.
FIG. 2 shows experimental results.
FIG. 3 shows x-ray diffraction patterns of obtained cobalt molybdate.

DETAILED DESCRIPTION OF THE PRESENT INVENTION

Molybdenum is included in a large number of very interesting materials in terms of industrial application view. The mixed oxide of molybdenum and samarium is proposed as a non-toxic pigment yellow (U.S. Pat. No. 8,303,706). A method of synthesis of the molybdenum oxide MoO3 is proposed in U.S. Pat. No. 7,829,060. Molybdenum oxide also provides a good host for network movement of lithium ions Li+. Therefore, a base electrode of molybdenum oxide has been developed for rechargeable batteries (U.S. Pat. No. 6,346,348). In the European patent EP 1666420 it is a composite CuMoO4 phase used in the manufacture of electronic components.

All these examples, just to name a few, are showing interest in materials based on molybdenum. In the patent literature no reference to molybdenum precursor is cited.

To illustrate the subject of this invention the following cases cited as non-limiting examples are presented.

Example 1

Preparation of the Molybdenum Oxide MoO3

In a first stage are ground in a mortar amounts of ammonium molybdate (NH4)6Mo7O24.4H2O and oxalic acid H2C2O4, 2H2O in the molar ratio Mo/acid=1/3. The mixture is then moistened in a crucible with a few drops of water on a hot plate at 150 degrees Celsius. The mixture turns deep blue color corresponding to the occurrence of reduced molybdenum phase. In this step two phenomena occur: the first is the reduction of molybdenum evidenced by the appearance of blue color and simultaneously the oxidation of oxalic acid according to the reaction:

$C_2O_4^{2-} \Longrightarrow 2CO_2 + 2e-$

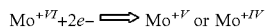

$Mo^{+VI} + 2e- \Longrightarrow Mo^{+V}$ or $Mo^{+IV}$

The second phenomenon is molybdenum complexation with oxalic acid to form oxalato complex which is in effect the precursor.

The precursor obtained will be treated in an oven for two hours at a temperature of 400 degrees Celsius to decompose and thereby obtain oxide MoO3 (JCPDS #85-2405) confirmed by the X-ray spectrum of FIG. 1.

A catalytic test was done with this oxide in the reduction reaction of the nitrophenol to produce the two 2-amino phenol in the presence of NaBH4. A reaction that takes place in a few hours without the use of the catalyst. A spectacular result is observed in our case the reaction takes only two minutes. The results of this experiment are presented in FIG. 2

Example 2

Preparation of Cobalt Molybdate CoMoO4

The same procedure is followed with the proportions Co/Mo/oxalic acid is 1/1/6. In this case the precursor is heated in the oven to 600 degrees. A single phase is obtained as it is confirmed by the analysis of powder X-ray diffraction (FIG. 3). It is cobalt molybdate CoMoO4 with JCPDS number: 21-0868. Measurements of the adsorption desorption curves gives a BET specific surface area of this material equal to 28.35 m2/g which corresponds to a particle size of approximately 30 nm. A result in itself is very interesting because the particles of the obtained oxide are in the nanometer scale.

It is thus proved that the precursors prepared by this method result in the form of oxides single phase.

Moreover, these precursors have the particularity to be very soluble in water and alcohols. This results in the ability to deposit thin film and opening an even wider field of application.

We present here a very simple and original molybdenum precursors synthesis. These precursor complexes are oxalic acid, tartaric acid or citric acid for example. They are prepared in situ which have the advantage:

to be intimately mixed with other metal complexes in order to prepare bi- or tri-metallic phases. This solves the problem of homogeneity of the material encountered in general synthesis methods. The intimate mixture of the metal complex or precursor initially give homogeneous materials.

These precursors are soluble in water and alcohols and offer the obtaining of thin films of materials containing molybdenum These precursors can also be used to prepare sulfides or nitrides materials under adequate conditions.

The invention gives a new issue where the precursor is a complex of reduced molybdenum(+IV or +V) with an intimate mixing of the elements before heat treating. This is an equal situation with the sol gel method or the coprecipitation method. It is avoiding the use of liquid solutions where we have to control the pH, the concentration, filtration and earning the operation time. This synthesis method consists in mixing the reactants in a mortar and then heating the mixture. No other steps are required.

One of the strengths of this invention is the possibility to prepare the materials on an industrial scale.

The invention claimed is:
1. A synthesis method, comprising:
   mixing ammonium molybdate with a polycarboxylic acid;
   heating the mixture to a temperature of about 150° C. to form a molybdenum oxide precursor;
   dissolving the molybdenum oxide precursor in water to form a molybdenum oxide precursor solution; and
   depositing the molybdenum oxide precursor solution on a substrate.
2. The synthesis method according to claim 1, wherein the ammonium molybdate and the polycarboxylic acid are ground together as solids.
3. The synthesis method according to claim 2, further comprising adding a small amount of water to the mixture, but not enough water to form a liquid solution.

4. The synthesis method according to claim 1, wherein the molar ratio of ammonium molybdate to polycarboxylic acid is about 1/3.

5. The synthesis method according to claim 1, wherein the polycarboxylic acid is selected from the group consisting of oxalic acid, tartaric acid and citric acid.

6. The synthesis method according to claim 5, wherein the polycarboxylic acid is oxalic acid.

7. The synthesis method according to claim 1, wherein the polycarboxylic acid acts as both a reducing agent and a complexing agent for the molybdenum.

8. The synthesis method according to claim 1, heating the molybdenum oxide precursor at a temperature from about 400 to about 1000° C. to form molybdenum oxide.

9. The synthesis method according to claim 1, further comprising mixing a metal salt with the ammonium molybdate and polycarboxylic acid to form a polymetallic material.

10. The synthesis method according to claim 9, wherein the metal salt contains cobalt.

11. The synthesis method according to claim 9, wherein the molybdenum oxide precursor is a molybdenum/polycarboxylic acid complex.

12. The synthesis method according to claim 9, wherein the complex formed is a complex of the metals used in the mixture or a mixture of each complex.

13. A synthesis method, comprising:
    mixing ground ammonium molybdate with a ground polycarboxylic acid;
    heating the mixture to a temperature of about 150° C. to reduce the molybdenum and form a molybdenum oxide precursor;
    dissolving the molybdenum oxide precursor in alcohol to form a precursor solution;
    depositing the precursor solution on a substrate; and
    heating the molybdenum oxide precursor at a temperature from about 400 to about 1000° C. to form a molybdenum-containing oxide.

14. The synthesis method according to claim 13, wherein the ammonium molybdate and the polycarboxylic acid are ground together as solids.

15. The synthesis method according to claim 14, further comprising optionally adding a small amount of water to the mixture, but not enough water to form a liquid solution.

16. The synthesis method according to claim 13, wherein the molar ratio of ammonium molybdate to polycarboxylic acid is about 1/3.

17. The synthesis method according to claim 13, wherein the polycarboxylic acid is selected from the group consisting of oxalic acid, tartaric acid and citric acid.

18. The synthesis method according to claim 17, wherein the polycarboxylic acid is oxalic acid.

19. The synthesis method according to claim 13, wherein the polycarboxylic acid acts as both a reducing agent and a complexing agent for the molybdenum.

20. The synthesis method according to claim 19, wherein the molybdenum-containing oxide is molybdenum oxide.

21. The synthesis method according to claim 13, further comprising mixing a metal salt with the ammonium molybdate and polycarboxylic acid to form a polymetallic oxide.

22. The synthesis method according to claim 21, wherein the metal salt contains cobalt and the molybdenum-containing oxide is cobalt molybdate.

23. The synthesis method according to claim 21, wherein the molybdenum oxide precursor is a molybdenum/polycarboxylic acid complex.

24. The synthesis method according to claim 21, wherein the complex formed is a complex of the metals used in the mixture or a mixture of each complex.

25. A method of forming a thin film of molybdenum oxide, comprising:
    mixing ground ammonium molybdate with a ground polycarboxylic acid;
    heating the mixture to a temperature of about 150° C. to reduce the molybdenum and form a molybdenum/polycarboxylic precursor;
    dissolving the molybdenum/polycarboxylic precursor in water or alcohol to form a molybdenum/polycarboxylic precursor solution;
    depositing the molybdenum/polycarboxylic precursor solution on a substrate; and
    heating the molybdenum/polycarboxylic precursor at a temperature from about 400 to about 1000° C. to form molybdenum oxide.

26. The method of claim 25, wherein the ammonium molybdate and the polycarboxylic acid are ground together as solids.

* * * * *